(12) United States Patent
Berkson (10) Patent No.: US 10,054,096 B2
(45) Date of Patent: Aug. 21, 2018

(54) VEHICLE OCCUPANT PROTECTION AND ENGINE IDLE REDUCTION SYSTEM

(71) Applicant: Bruce Richard Berkson, Sedona, AZ (US)

(72) Inventor: Bruce Richard Berkson, Sedona, AZ (US)

(73) Assignee: N4 INNOVATIONS, LLC, Scottsdale, AZ (US)

( * ) Notice: Subject to any disclaimer, the term of this patent is extended or adjusted under 35 U.S.C. 154(b) by 1 day.

(21) Appl. No.: 14/861,883

(22) Filed: Sep. 22, 2015

(65) Prior Publication Data

US 2016/0090958 A1    Mar. 31, 2016

Related U.S. Application Data

(60) Provisional application No. 62/071,519, filed on Sep. 25, 2014.

(51) Int. Cl.

| | |
|---|---|
| *F02N 11/08* | (2006.01) |
| *B60H 1/00* | (2006.01) |
| *F02N 11/04* | (2006.01) |
| *G01N 33/00* | (2006.01) |

(52) U.S. Cl.
CPC ......... *F02N 11/0833* (2013.01); *B60H 1/008* (2013.01); *B60H 1/00978* (2013.01); *F02N 11/04* (2013.01); *F02N 2200/08* (2013.01); *F02N 2200/0803* (2013.01); *G01N 33/004* (2013.01); *Y02T 10/48* (2013.01)

(58) Field of Classification Search
CPC .. F02N 11/04; F02N 11/0833; F02N 2200/08; F02N 2200/0803; G01N 33/004; B60H 1/00

USPC .............. 123/179.4, 179.13, 198 D, 198 DB, 123/196 S, 196 AB; 701/102, 106, 112, 701/114
See application file for complete search history.

(56) References Cited

U.S. PATENT DOCUMENTS 4,653,601 A * 3/1987 Nakamura ........... B62D 5/0457
                                                          180/446
5,276,434 A * 1/1994 Brooks ................ G08B 21/14
                                                          340/632

(Continued)

*Primary Examiner* — John Kwon
*Assistant Examiner* — Johnny H Hoang
(74) *Attorney, Agent, or Firm* — Kelly & Kelley, LLP (57) ABSTRACT

A system for automatically adjusting the temperature and carbon monoxide level in an occupied passenger compartment of a vehicle includes sensors for sensing carbon monoxide levels, temperature, and occupants in the passenger compartment. A controller receives input from the sensors, and activates an electric heater or an electric cooler to bring the temperatures within the passenger compartment within a predetermined temperature range if the temperature detected within the passenger compartment falls outside of the predetermined range of temperatures. The controller may automatically shut off the engine of the vehicle when the vehicle is in idle and the carbon monoxide level within the passenger compartment falls above a predetermined level, or if a transmission lever of the vehicle is placed in a park position. A motor generator unit coupled to the engine provides electricity to rechargeable batteries of an alternate power unit, which powers the electric heater and the electric cooler.

29 Claims, 7 Drawing Sheets

(56) References Cited

U.S. PATENT DOCUMENTS

| | | | |
|---|---|---|---|
| 6,057,755 A * | 5/2000 | Phillips | G08B 21/14 180/271 |
| 6,072,398 A * | 6/2000 | Hayes | G08B 17/117 180/271 |
| 6,208,256 B1 * | 3/2001 | Fleming | B60K 28/066 180/271 |
| 6,672,954 B2 * | 1/2004 | Shtanko | B60H 1/00264 454/131 |
| 7,430,469 B2 * | 9/2008 | Kaita | B60K 6/445 123/516 |
| 7,610,895 B2 * | 11/2009 | Klingebiel | F01P 7/167 123/299 |
| 7,690,075 B2 * | 4/2010 | Cunningham | A47L 5/38 15/301 |
| 7,808,118 B2 | 10/2010 | Berkson | |
| 7,970,528 B2 * | 6/2011 | Janarthanam | B60H 1/008 123/321 |
| 8,170,779 B2 * | 5/2012 | Iwase | F01N 5/02 123/142.5 R |
| 2002/0121967 A1 * | 9/2002 | Bowen | B60Q 1/52 340/425.5 |
| 2006/0011337 A1 * | 1/2006 | Paul | B60H 1/00907 165/240 |
| 2009/0271088 A1 * | 10/2009 | Langham | F01B 11/004 701/102 |
| 2011/0087390 A1 * | 4/2011 | Pandit | B60K 1/00 701/22 |
| 2012/0310547 A1 * | 12/2012 | Cristoforo | G08B 21/14 702/24 |
| 2014/0283764 A1 * | 9/2014 | Abou-Nasr | F01P 7/162 123/41.02 |
| 2014/0319957 A1 * | 10/2014 | Hao | H02K 17/16 310/211 |
| 2015/0149008 A1 * | 5/2015 | Jang | B60W 20/30 701/22 |
| 2015/0210284 A1 * | 7/2015 | Miyashita | B60W 40/04 701/117 |
| 2015/0217761 A1 * | 8/2015 | Christman | B60W 20/40 701/22 |
| 2015/0258984 A1 * | 9/2015 | Atluri | B60W 10/06 701/22 |
| 2015/0298688 A1 * | 10/2015 | Teraya | B60L 1/006 701/22 |
| 2015/0367835 A1 * | 12/2015 | Ikedaya | B60W 10/06 701/22 |
| 2016/0011275 A1 * | 1/2016 | Saito | F02N 11/0862 324/430 |
| 2016/0059843 A1 * | 3/2016 | Oguma | B60W 20/14 701/22 |
| 2016/0063771 A1 * | 3/2016 | Meyer | G07C 5/004 701/123 |
| 2016/0114652 A1 * | 4/2016 | Izumi | B60H 1/3208 701/36 |
| 2016/0153374 A1 * | 6/2016 | Tashiro | F02D 41/10 701/103 |
| 2016/0185461 A1 * | 6/2016 | Beuning | B64D 41/00 244/58 |
| 2016/0236540 A1 * | 8/2016 | Ikeda | B60W 10/00 |
| 2016/0258409 A1 * | 9/2016 | Marthaler | F02N 11/003 |

* cited by examiner

VEHICLE OCCUPANT PROTECTION AND ENGINE IDLE REDUCTION SYSTEM

RELATED APPLICATION

This application claims the benefit of U.S. Provisional Application No. 62/071,519, filed on Sep. 25, 2014.

BACKGROUND OF THE INVENTION

The present invention is generally related to vehicle HVAC and idle reduction systems. More particularly, the present invention is directed to a system for automatically adjusting the temperature and carbon monoxide levels in an occupied passenger compartment of the vehicle in order to protect occupants thereof, as well as reducing unnecessary idling of the engine of the vehicle, while providing hybrid electric drive power to the engine crankshaft.

Studies reveal that vehicles which idle for prolonged periods of time, including, but not limited to, police vehicles, taxis, limousines, construction and utility trucks, burn thousands of gallons of fuel each year while idling. In many cases, idle times exceed drive times. The resulting wasted fuel and added maintenance costs are very high. It is well known in the trade that the damage to diesel engines caused by piston slap that results from long diesel engine idling is significant. As a result, costly diesel engine rebuilds are frequently required for prolonged-idle vehicles.

It has been found to be cost effective to develop idle reduction strategies that turn off the engine any time the vehicle is at rest and in a state of prolonged idle. However, experience has shown drivers often won't voluntarily turn off their air conditioning or heater when temperatures become uncomfortable and/or potentially unsafe.

Drivers of prolonged-idle vehicles, including police, taxis, limousines, construction and utility companies and the like, often use their radios, lights, heaters, air conditioning and other accessories while idling. These added accessories overload the original equipment manufacturers' (OEM) 12-volt electric systems and cause the batteries, starters and alternators to experience extremely high failure rates. When the OEM electrical system is also used to recharge an idle reduction system, idle reduction system batteries and idle electric system failure also frequently occurs. As a result, prolonged-idle vehicles with or without other idle reduction systems are often left inoperable.

Police vehicles which idle to power their accessories pose a significant security and safety risk when the vehicle must be left running, particularly when the driver must exit the vehicle. Police agencies have reported numerous accidental deaths of children, pets and K9 officers who were inadvertently left unattended in overheated vehicles.

Previous idle reduction systems and methods do not automatically activate thermal or carbon monoxide occupant protection when a passenger occupies the vehicle. Previous idle reduction systems and methods do not integrate electric air conditioning or electric space heating with the OEM HVAC systems. Previous idle reduction systems typically exceed 12-volt electrical system capacities, and do not provide autonomous charge-sustaining operation.

It is well known that the distributed electric infrastructure required to recharge fleets of hybrid or electric vehicles is virtually non-existent. It is also well known that the cost to install large distributed electric recharging systems is extremely expensive. Previous idle reduction systems do not provide charge-sustaining operation, and previous vehicles using electric air conditioning are susceptible to motor controller failure due to high operating temperatures.

Accordingly, there is a continuing need for a system and method for automatically monitoring and adjusting the temperature and carbon monoxide level in an occupied passenger compartment of a vehicle. There is also a continuing need for reducing prolonged idle states of vehicles, while providing protection of the occupants of the vehicle. There is also a continuing need for added power and fuel efficiency derived from hybrid electric drive. The present invention fulfills these needs, and provides other related advantages.

SUMMARY OF THE INVENTION

The present invention resides in a system for automatically adjusting the temperature and carbon monoxide level in an occupied passenger compartment of a vehicle. The system and method of the present invention can also be used to prevent unnecessary engine idling and provide fuel savings.

The system of the present invention generally comprises a sensor for sensing carbon monoxide levels in the passenger compartment. A sensor also senses the temperature in the passenger compartment. Typically, at least one sensor also senses that a living occupant is within the passenger compartment. A controller receives input from the carbon monoxide sensor and the temperature and monitors the carbon monoxide levels and the temperature within the passenger compartment. If the temperature within the passenger compartment falls outside of a predetermined range of temperatures, the controller activates an electric heater or an electric cooler to bring the temperatures within the passenger compartment within the predetermined temperature range. When the vehicle is in idle and the carbon monoxide level within the passenger compartment falls above a predetermined level, the controller shuts off an engine of the vehicle and activates the climate control system to flush out the contaminated air from the passenger compartment.

The controller may automatically shut off the engine when a transmission lever of the vehicle is placed in the park position. The controller automatically restarts the engine when an accelerator pedal of the vehicle is depressed. The engine may also be manually restarted by the ignition switch.

In addition to a primary alternator coupled to the engine, a motor generator unit that generates electricity is coupled to the engine, in accordance with the invention. The motor generator unit may be installed on the engine and coupled to belts of the engine in lieu of the mechanical air conditioning compressor.

In addition to a battery electrically coupled to the primary alternator for starting the engine of the vehicle, the present invention provides an alternate power unit comprising rechargeable batteries electrically coupled to the motor generator unit. The electric heater and the electric cooler receive electricity from either the alternate power unit or the motor generator unit. Electrically-powered lights and accessories of the vehicle may also receive electricity from either the alternate power unit or the motor generator unit.

The controller automatically starts the engine when levels of electrical charge in the batteries of the alternate power unit are detected below a predetermined level.

The motor generator unit may supply power to a crankshaft of the engine, such as when the batteries of the alternate power unit are fully charged or when the batteries of the alternate power unit and other electrically-powered lights and accessories of the vehicle do not require the full capacity of the motor generator unit.

The electric cooler (compressor) is preferably disposed within an enclosure that is cooled by a low pressure refrigerant line of the electric cooler which is at least partially disposed within the enclosure. The high pressure refrigerant line of the electric cooler (compressor) is disposed outside of the enclosure. The cool air from the enclosure may be directed to the alternate power unit, to the motor controller of the compressor, to a power generating device appurtenant to the exhaust from a catalytic converter of the vehicle, or a forced cold air induction manifold of the engine. The enclosure may be configured to shield electromagnetic signals and noise emissions.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

As shown in the accompanying drawings, for purposes of illustration, the present invention is directed to a system and method for automatically adjusting environmental conditions, including temperature and carbon monoxide levels, in an occupied passenger compartment of a vehicle. The system and method of the present invention can also reduce or even eliminate periods of prolonged vehicle idling. The present invention can also prolong the usable life of components of a conventional vehicle, and thus result in cost savings due to maintenance, replacement of parts, and fuel.

Figure 1:
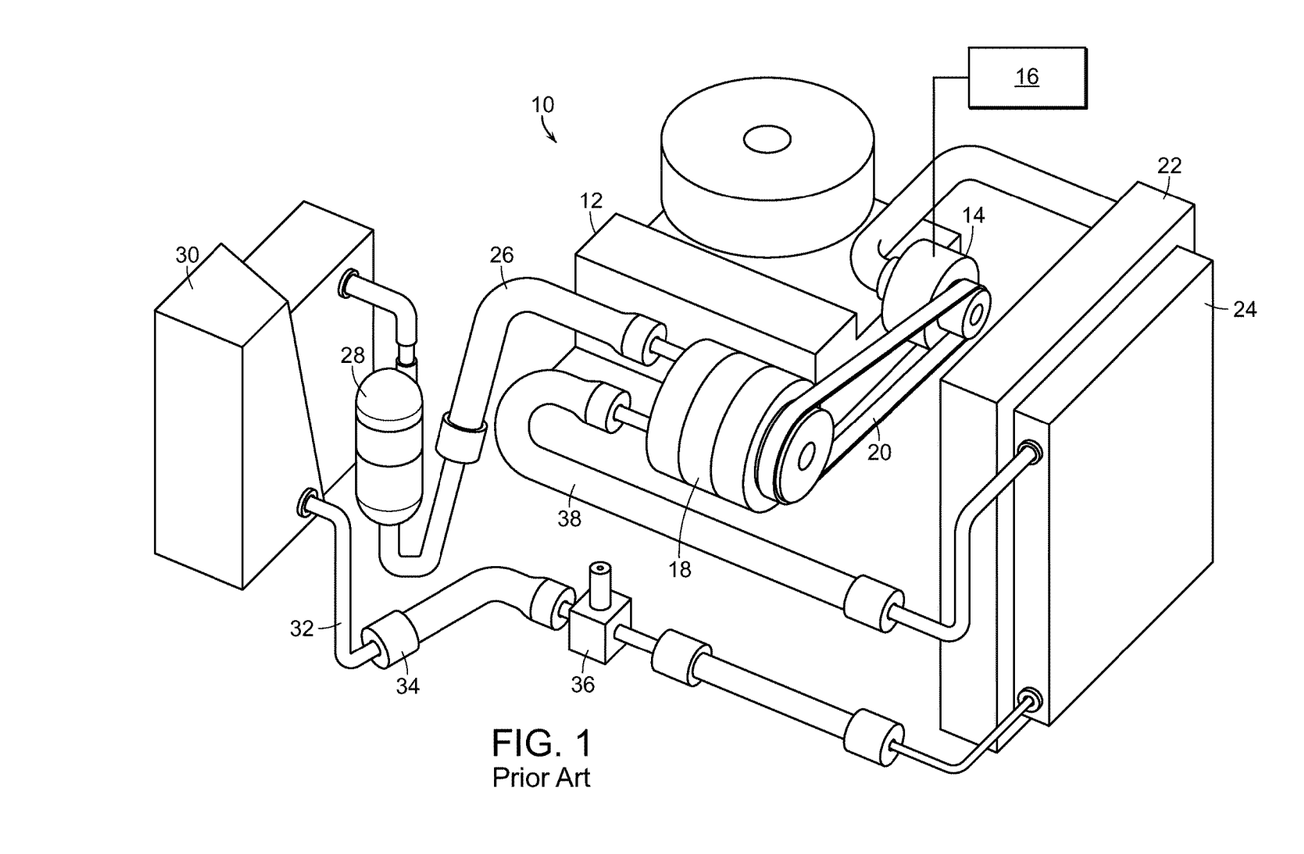
FIG. 1 is a schematic diagram illustrating a conventional engine arrangement in accordance with the prior art which incorporates a mechanical air conditioning compressor.

With reference now to FIG. 1, a conventional engine 10, typically an internal combustion engine, is shown. The engine 10 includes an engine block 12 having the typical pistons, crankshafts, camshafts, and the like. An alternator 14 is typically mounted onto the engine block and generates electricity for charging the vehicle's battery 16, typically a 12-volt battery. A mechanical air conditioning compressor 18 is also mounted to, or otherwise associated with, the engine 10 for creating cool air, as is known in the art. A system of belts and pulleys 20 impart rotational energy from shafts of the engine 10 to the alternator 14 and the mechanical air conditioning compressor 18 in order to operate these components, as is known in the art.

As is well known in the art, engines typically have a radiator 22 and a condenser 24 for thermal management of the engine and its components.

In order to provide cool, conditioned air to the passenger compartment of the vehicle, refrigerant, such as Freon®, is compressed by the mechanical air conditioning compressor 18 passed through tubing 26 to an accumulator 28 where it is then passed to an evaporator 30, where the evaporation of the compressed refrigerant creates a thermal condition where cool air can be generated. The evaporated refrigerant is then passed through tubing 32, through one or more orifices 34, a refrigerant charge tube 36, and then onto the condenser 24, before being returned via tubing 38 to the mechanical air conditioning compressor 18.

Heated air is provided from heat generated by the engine and/or radiator 22 and piped into the passenger compartment, through filters, as desired.

In order to create and direct cooled or heated air into the passenger compartment of the vehicle, the engine must be running. Thus, there are many situations where when a vehicle is parked the driver of the vehicle leaves the engine idling so as to maintain the desired temperature within the passenger compartment of the vehicle. This requires expenditure of fuel and the operation of the aforementioned components. Moreover, in certain situations carbon monoxide levels within the passenger compartment can become elevated, posing a danger and threat to the occupants of the passenger compartment, when the vehicle is idling.

Figure 2:
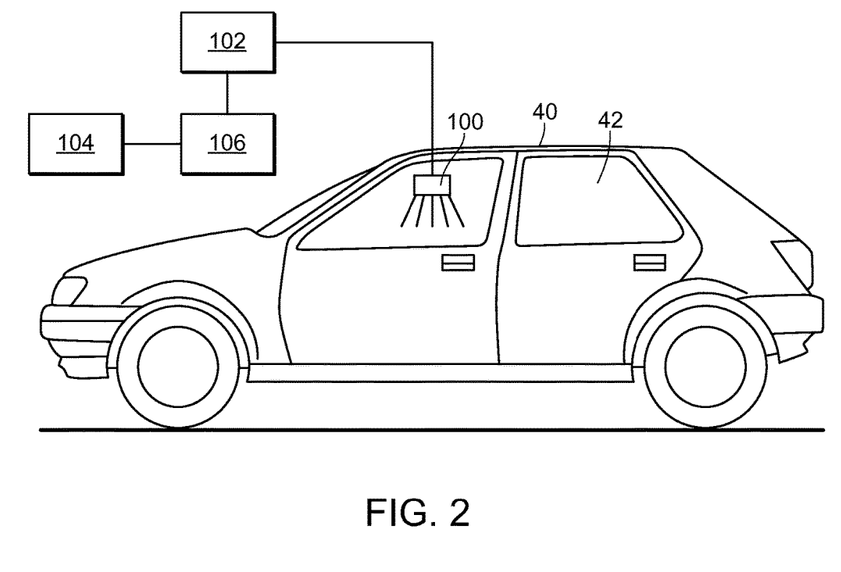
FIG. 2 is a diagrammatic view of a vehicle having sensors detecting conditions in an occupant occupied compartment thereof, in accordance with the present invention.

With reference now to FIG. 2, a vehicle 40 is illustrated. It will be appreciated that the vehicle 40 can comprise any type of passenger vehicle, typically including an automobile in the form of a car, truck, and the like. The vehicle 40 has therein a passenger compartment 42 where the driver sits to operate the vehicle 40 and passengers may be seated, as is well known.

In accordance with the present invention, one or more sensors 100 sense and detect parameters and conditions within the passenger compartment 42. Such sensors include a sensor for sensing carbon monoxide levels in the passenger compartment, a sensor for sensing the temperature in the passenger compartment of the vehicle, and a sensor for detecting the presence of a living occupant within the passenger compartment. The detection of a living occupant within the passenger compartment 42 can be by means of a motion detector, an infrared sensor, pressure sensors in the seats of the vehicle, or any other sensor which could detect that an occupant is within the passenger compartment 42 of the vehicle 40.

A controller 102 is operably connected to the one or more sensors 100. The controller 102 is also operably coupled to an electric heating system 104 and an electric cooling system 106 embodying the present invention. If the temperature within the passenger compartment 42 is detected as falling outside of a predetermined range of temperatures, the controller 102 activates either the electric heating system 104 or the electric cooling system 106 to bring the temperatures within the passenger compartment within the predetermined temperature range. The controller 102 is also operably connected to the engine 10 such that it can shut off the engine when the sensors 100 detect that the carbon monoxide level within the passenger compartment 42 falls above a predetermined level. The controller 102 may also be used to shut off the engine and prevent it from idling unnecessarily. The invention contemplates the automatic restart of the engine, such as when the driver depresses the gas pedal of the vehicle.

Figure 3:
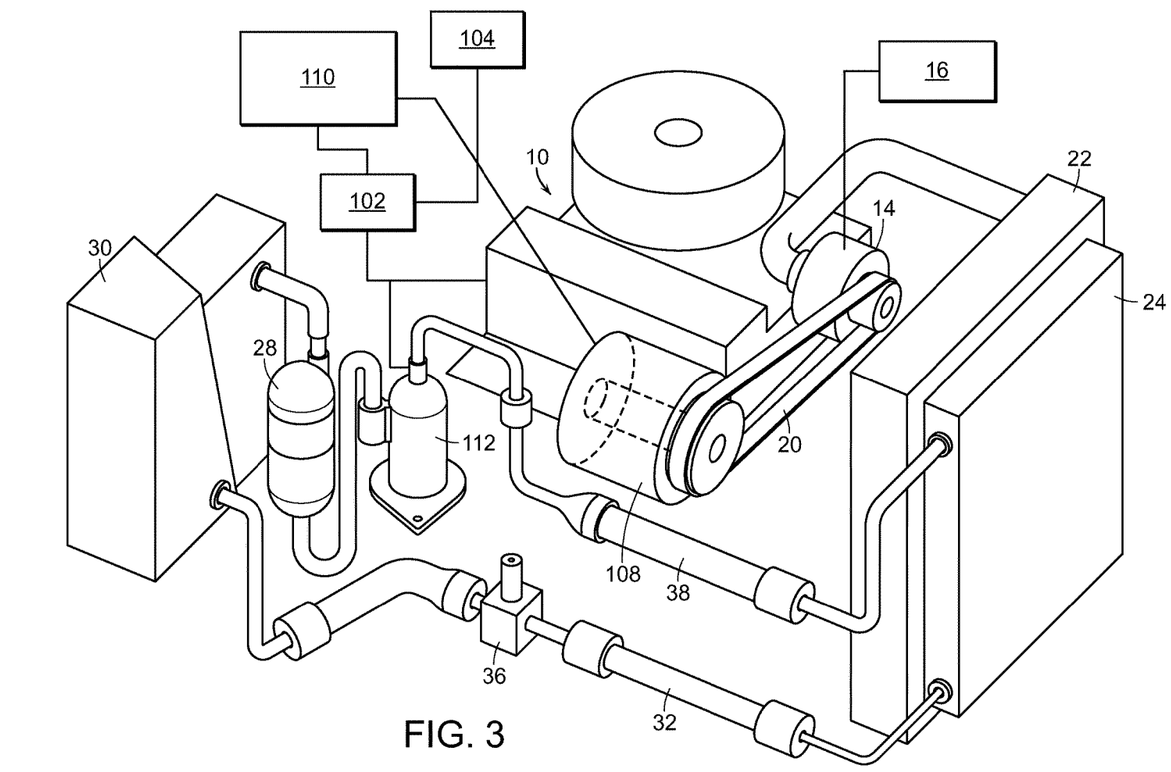
FIG. 3 is a diagrammatic illustration similar to FIG. 1, but incorporating the present invention therein.

With reference now to FIG. 3, in accordance with the present invention, various components of a conventional engine 10 are changed, either at the time of manufacturing or as a process of retrofitting the engine 10 to incorporate the system of the present invention. In place of the mechanical air conditioning compressor 18, a motor generator unit 108 is installed. The motor generator unit 108 may be attached to the engine 10 using the same bracket provided with the mechanical air conditioning compressor 18, a mounting bracket which is specific to the engine type, or a universal bracket. It can be seen that the motor generator unit 108 is coupled to the belt system 20 of the engine. The motor generator unit 108 generates electricity for charging rechargeable battery cells of an alternate power unit 110. The motor generator unit 108 may comprise a second alternator.

The alternate power unit 110 is operably coupled to the controller 102, and electrically coupled to the motor generator unit 108. The alternate power unit 110 is used to provide electricity to the electric heating system 104 and the electric cooling system 106 of the present invention. Preferably, electrically-powered lights and other accessories of the vehicle 40 are also powered by the alternate power unit 110. This enables the original equipment manufacturing (OEM) battery 16 and alternator 14 to be dedicated to starting the engine, and thus prolonging their usable lives.

When the battery cells of the alternate power unit 110 are fully charged, the invention contemplates the motor generator unit 108 diverting power to the engine, such as a crankshaft of the engine, so as to conserve fuel. As such, the motor generator unit 108 is interactively connected to the alternate power unit, such as being monitored and controlled by the controller 102, wherein it either charges the APU or returns hybrid electric power back to the crankshaft through an idler pulley belt, for example.

When an occupant of any type, size or weight is located within the vehicle, which can include adults, children, or even pets, the sensors 100 detect the presence of the occupants and automatically activate the thermal climate control systems 104 and/or 106 of the present invention. If the engine is running and the vehicle is moving, the OEM heating system may be used to heat the passenger compartment. This can also be the case when the vehicle is parked and in idle, and the system of the present invention does not detect abnormal levels of carbon monoxide and the engine is not automatically shut off. However, in the case when the engine is shut off, such as the present invention automatically shutting off the engine to conserve fuel, such as when a transmission lever of the vehicle is put into the park position, an electric heater 104 powered by the alternate power unit 110 may be used to provide heat, as necessary, to the passenger compartment 42. For example, electric heat strips may be placed in the heater vents and powered by the alternate power unit (APU) 110.

With reference again to FIG. 3, as described above, the mechanical air conditioning compressor which is conventionally used in engines is removed and replaced with the motor generator unit (MGU) in accordance with the present invention. Instead, an electric cooler 112, in the form of an electric air conditioning compressor receives electric power from the alternating power unit 110 or motor generator unit 108 and is operably controlled by the controller 102 so as to automatically be activated when the temperature in the passenger compartment of the vehicle falls above a predetermined range of temperatures. The electric air conditioning compressor 112 may utilize an infinitely variable thermostat to adjust for passenger compartment temperature. Preferably, a lower temperature limit is set, such as at 60° F., from the vent in order to prevent the refrigerant from reaching its boiling point within the system.

The incorporation of the motor generator unit 108 and the electric air conditioning compressor or cooler 112 requires a different plumbing arrangement, as illustrated in FIG. 3. Tubing 38 extends between the electric cooler 112 and the condenser 24. The electric cooler 112 is fluidly coupled to the accumulator 28.

Figure 4:
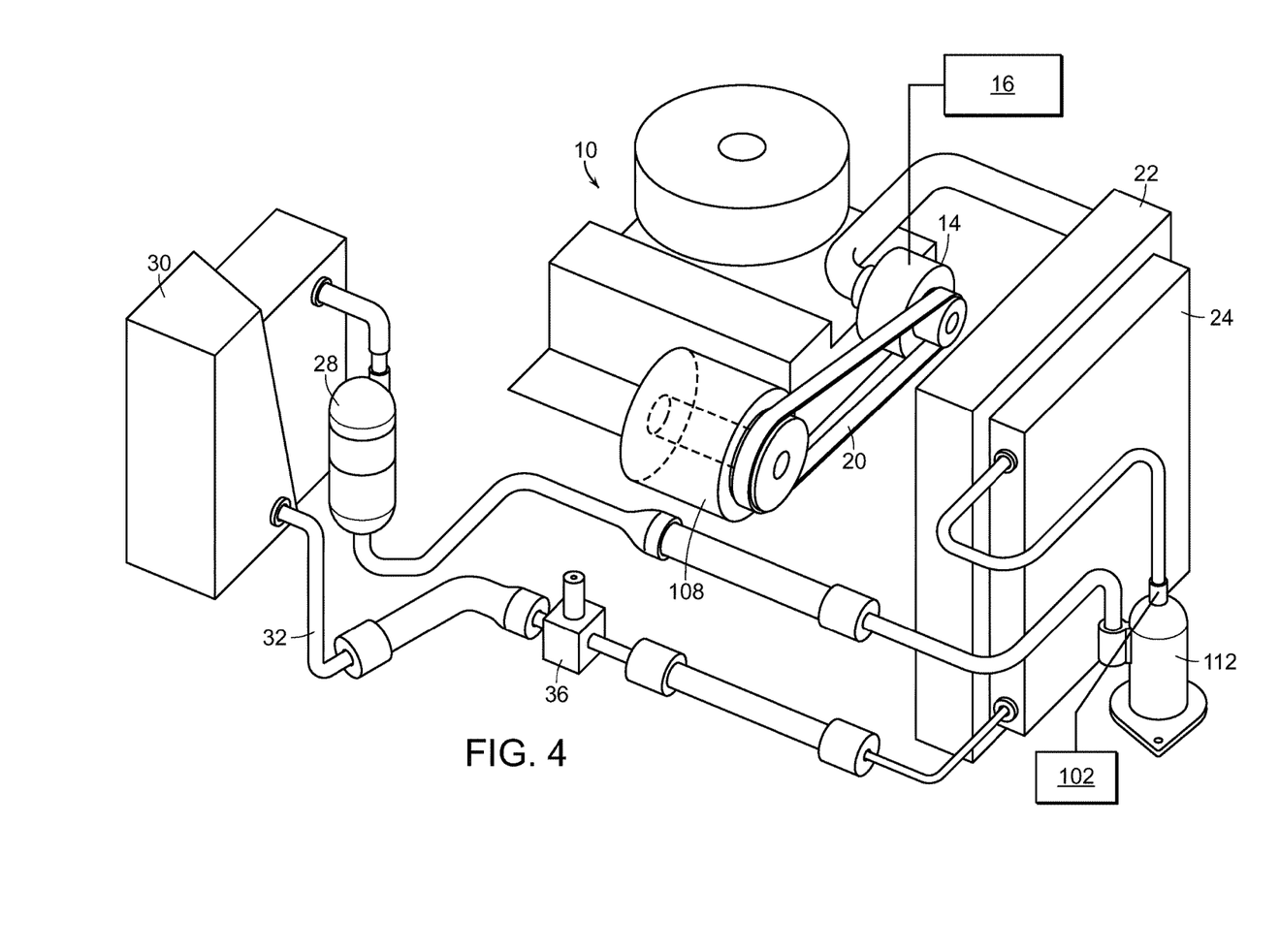
FIG. 4 is a diagrammatic view of a system embodying the present invention.

With reference now to FIG. 4, the electric cooler 112 and the arrangement of the piping and tubing can be adjusted depending upon the configuration and space parameters of each individual vehicle and engine. In this case, the electric cooler or electric air conditioning compressor 112 is disposed adjacent to the condenser 24. When retrofitting an existing engine, the air conditioning refrigerant lines are properly drained and capped, while the mechanical air conditioning compressor of the factory HVAC system is removed and capped so that the MGU 108 can be installed in its place. Thereafter, the air conditioning lines are rerouted to the electric air conditioning compressor cooler 112, as illustrated and described above.

Figure 5:
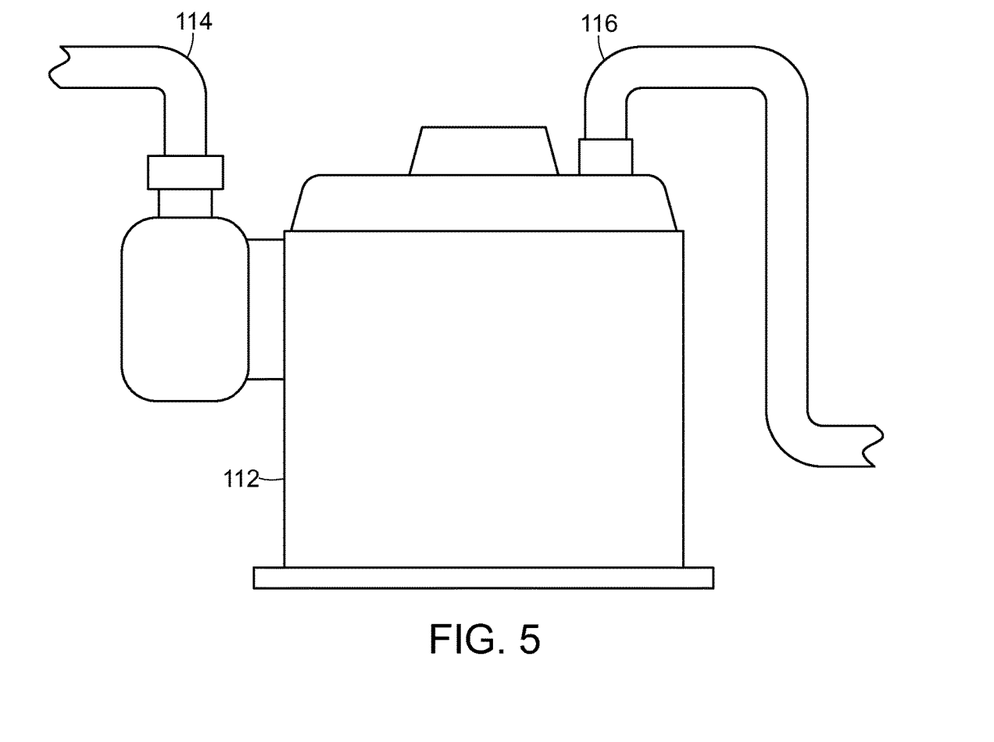
FIG. 5 is a diagrammatic view of an electric air conditioning cooler, embodying the present invention.
Figure 6:
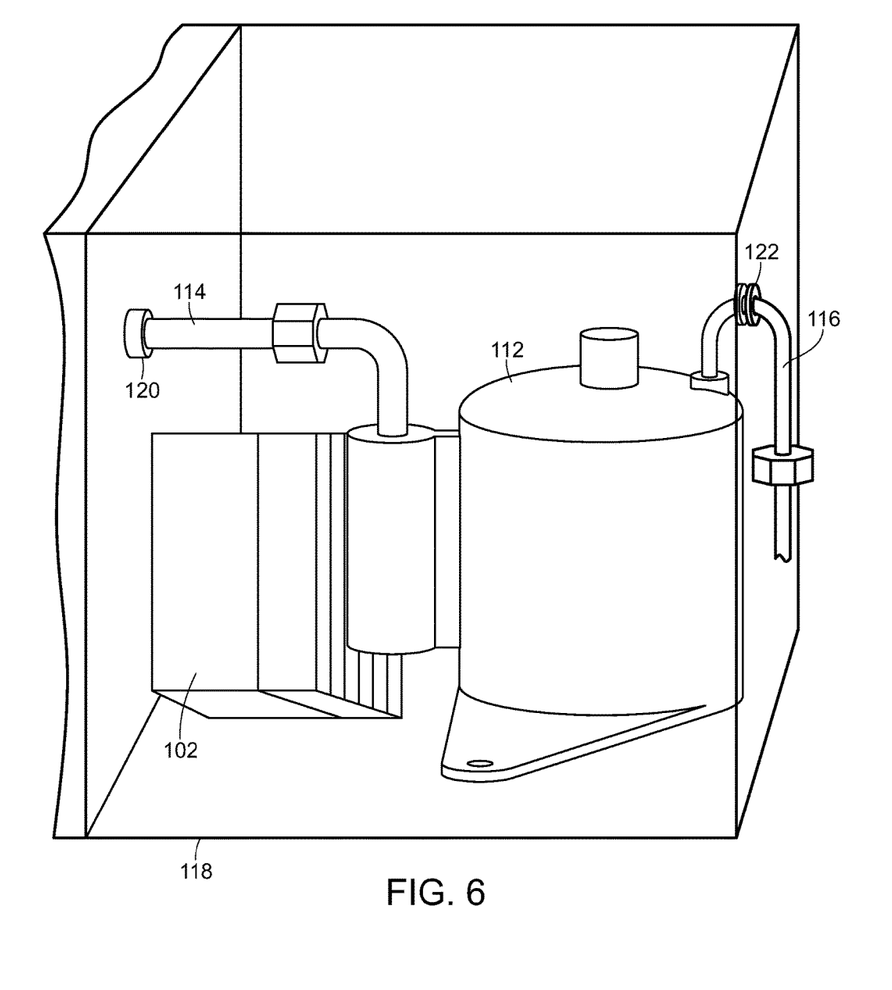
FIG. 6 is a diagrammatic view of an enclosure formed around electric cooler components, in accordance with the present invention.

With reference now to FIG. 5, an electric air conditioning compressor cooler 112 is shown with its low pressure inlet line 114 and its high pressure outlet line 116 coupled thereto. It is known that the low pressure inlet line 114 is cold, whereas the high pressure outlet line 116 is relative hot. With reference now to FIG. 6, the thermal dynamic differences between the inlet and outlet lines 114 and 116 may be advantageously used in the present invention. As illustrated in FIG. 6, the electric air conditioning compressor cooler 112 and at least a portion of the cold low pressure inlet line or tube 114 are placed within an enclosure 118. A seal 120 prevents cool air from leaving the enclosure 118 where the inlet line 114 passes therein, and another seal 122 is disposed where the high pressure outlet line 116 exits the enclosure 118, to prevent heat from transferring into the enclosure 118. The air is automatically cooled within the enclosure 118, due to the passing of air over the cold low pressure inlet line 114. Temperature-sensitive components, such as the controller 102 can be placed within the enclosure 118 to improve their operation and longevity and reliability.

Figure 7:
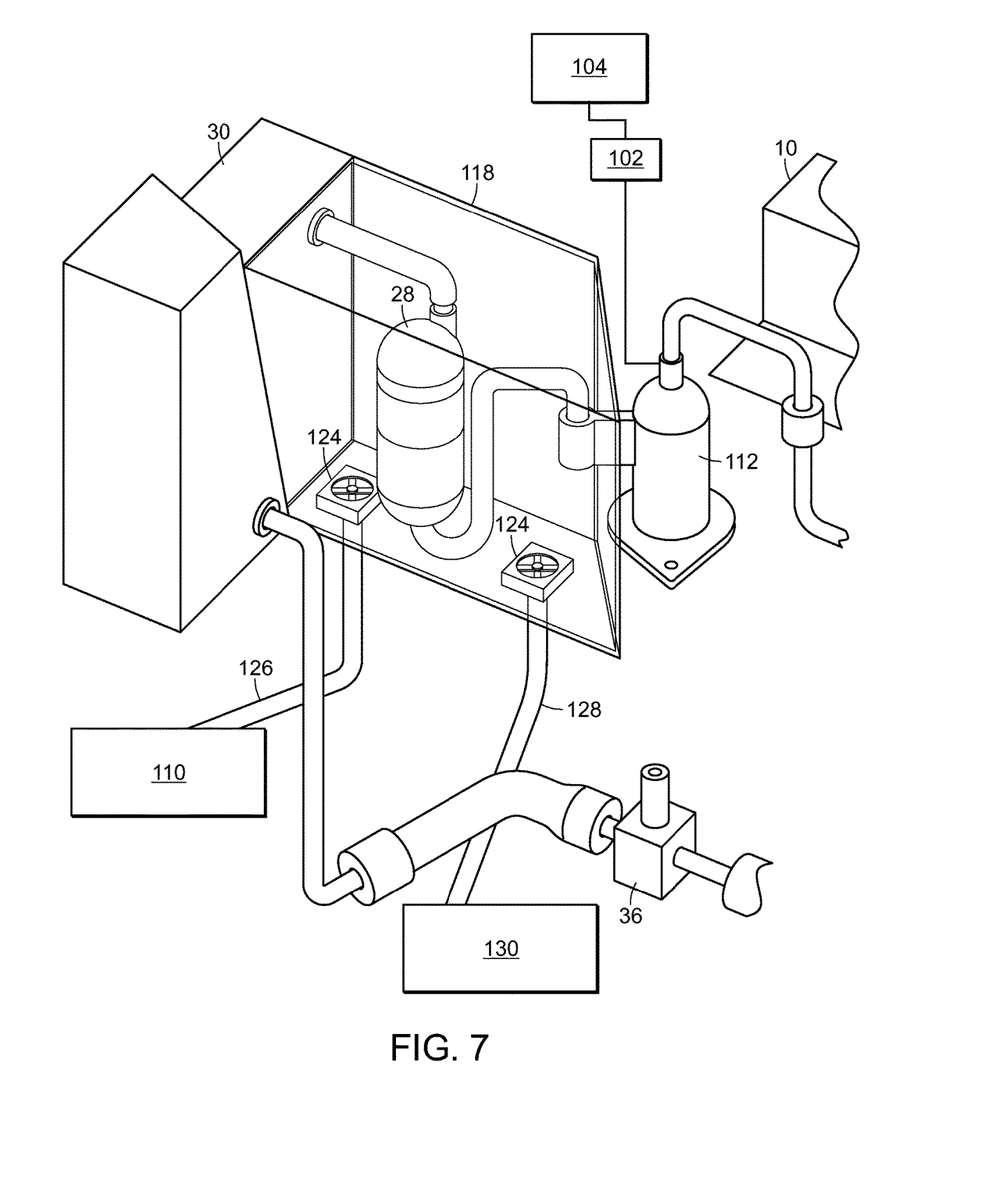
FIG. 7 is a diagrammatic view illustrating components of the system of the present invention.

With reference now to FIG. 7, the enclosure 118 is disposed around tubing and components of the cooling system which provide cool air within the enclosure 118. Instead of placing temperature-sensitive components within the enclosure 118, which may not be practical, fans 124, or pumps or other air moving devices, can transport cool air from the enclosure 118 to temperature-sensitive components. For example, the battery cells of the alternate power unit can be temperature sensitive and operate more reliably and efficiently at a cooler temperature. Thus, cool air is pushed by fan 124 through tubing 126 to the alternate power unit 110. The alternate power unit, or at least the rechargeable battery cells thereof, may be encased in its own enclosure where the cool air is piped into. Alternatively, or additionally, the cool air from the enclosure 118 may be transferred, such as via tubing 128, to another location 134 for advantageous use in the vehicle's operation, such as a power generating device appurtenant to the exhaust from a catalytic converter of the vehicle such that the exhaust exiting the vehicle is more environmentally friendly and contributes less to the greenhouse environmental effects, or to a forced cold air induction manifold of the engine, or the like.

The enclosure 118 may be placed in any convenient location around the cold low pressure refrigerant lines at any point to be optimally determined and located, such as around the accumulator, between the evaporator accumulator 28, between the evaporator core 30 and the low pressure inlet line of the electric air conditioning compressor 112, as illustrated in FIG. 7. The cold air from the enclosure 118 may also be used to partial motive power a Sterling Cycle Engine, as disclosed in U.S. Pat. No. 7,808,118, the contents of which are incorporated by reference herein. The enclosure 118 may also serve to shield components therein from electromagnetic signals and audible noise emissions generated by operation of the vehicle. A secondary controller can be disposed within the enclosure 118, as illustrated in FIG. 6, to provide system control redundancy and improve reliability.

Although several embodiments have been described in detail for purposes of illustration, various modifications may be made without departing from the scope and spirit of the invention. Accordingly, the invention is not to be limited, except as by the appended claims.

What is claimed is:

1. A system for automatically adjusting a temperature in a passenger compartment of a vehicle, comprising:
   a primary alternator coupled to an engine of the vehicle and electrically coupled to an engine starting battery of the vehicle;
   a motor generator unit that generates electricity and is coupled to belts of the engine in place of a mechanical air conditioning compressor;
   an alternate power unit comprising rechargeable batteries electrically coupled to the motor generator unit;
   an electric cooler electrically coupled to both the alternate power unit and the motor generator unit such that when the engine is running electricity is received from the motor generator unit, and when the engine is not running electricity is received from the alternate power unit;
   a temperature sensor for sensing the temperature in the passenger compartment; and
   a controller operably connected to the temperature sensor for monitoring and controlling the temperature within the passenger compartment, and further operably connected to the engine of the vehicle;
   wherein if the temperature within the passenger compartment falls outside of a predetermined range of temperatures, the controller activates a heater or the electric cooler to bring the temperatures within the passenger compartment within the predetermined temperature range.

2. The system of claim 1, wherein electrically-powered lights and accessories of the vehicle are electrically connected to and receive electricity from the alternate power unit and the motor generator unit.

3. The system of claim 1, wherein the controller automatically starts the engine when levels of electrical charge in the batteries of the alternate power unit are detected below a predetermined level.

4. The system of claim 1, wherein the controller automatically shuts off the engine when a transmission lever of the vehicle is placed in a park position.

5. The system of claim 4, wherein the controller automatically restarts the engine when an accelerator pedal of the vehicle is depressed.

6. The system of claim 1, wherein the motor generator unit supplies power to a crankshaft of the engine.

7. The system of claim 1, including a sensor operably connected to the controller for sensing that a living occupant is within the passenger compartment.

8. The system of claim 7, wherein the living occupant sensor comprises a motion detector or infrared sensor.

9. The system of claim 1, including a carbon monoxide sensor for detecting carbon monoxide levels within the passenger compartment, wherein the controller is operably connected to the carbon monoxide sensor for monitoring carbon monoxide levels, and when the vehicle is in idle and the carbon monoxide level within the passenger compartment exceeds a predetermined level, the controller shuts off the engine of the vehicle.

10. The system of claim 1, wherein the engine starting battery is used to only start the engine, and the primary alternator is dedicated to supplying electricity to the engine starting battery.

11. The system of claim 1, wherein the heater comprises an electric heater electrically connected to the alternate power unit and which does not require the engine to be running to operate.

12. A system for automatically adjusting a temperature and carbon monoxide level in an occupied passenger compartment of a vehicle, comprising:
   a primary alternator coupled to an engine of the vehicle;
   a battery electrically coupled to the primary alternator for starting an engine of the vehicle;
   a motor generator unit for generating electricity coupled to the engine in lieu of a mechanical air conditioning compressor;
   an alternate power unit comprised of rechargeable batteries electrically coupled to the motor generator unit;
   a carbon monoxide sensor for sensing carbon monoxide levels in the passenger compartment;
   a temperature sensor for sensing the temperature in the passenger compartment;
   a living occupant sensor for sensing that a living occupant is within the passenger compartment;
   a controller operably connected to the living occupant sensor, the carbon monoxide sensor and the temperature sensor for monitoring the carbon monoxide levels and the temperature within the passenger compartment, and further being operably connected to the engine of the vehicle;
   wherein if the temperature within the passenger compartment falls outside of a predetermined range of temperatures, the controller activates a heater or an electric cooler electrically coupled to the motor generator unit and the alternate power unit, to bring the temperature within the passenger compartment within the predetermined temperature range; and
   wherein when the vehicle is in idle and the carbon monoxide level within the passenger compartment exceeds a predetermined level, the controller shuts off the engine of the vehicle and activates a ventilation system that flushes contaminated air from the passenger compartment.

13. The system of claim 12, wherein the controller automatically starts the engine when levels of electrical charge in the batteries of the alternate power unit are detected below a predetermined level.

14. The system of claim 12, wherein the electric cooler is disposed within an enclosure that is cooled by a low pressure refrigerant line of the electric cooler at least partially disposed within the enclosure, and wherein cool air from the enclosure is directed to the alternate power unit, exhaust from a catalytic converter of the vehicle or a forced cold air induction manifold of the engine.

15. The system of claim 12, wherein the controller automatically shuts off the engine when a transmission lever of the vehicle is placed in a park position, and automatically restarts the engine when an accelerator pedal of the vehicle is depressed.

16. The system of claim 12 wherein the living occupant sensor comprises a motion detector or infrared sensor.

17. The system of claim 12, wherein the engine starting battery is used to only start the engine, and the primary alternator is dedicated to supplying electricity to the engine starting battery.

18. The system of claim 12, wherein the heater comprises an electric heater electrically connected to the alternate power unit and which does not require the engine to be running to operate.

19. A system for automatically adjusting a temperature in a passenger compartment of a vehicle, comprising:
- a primary alternator coupled to an engine of the vehicle and electrically coupled to an engine starting battery of the vehicle;
- a motor generator unit that generates electricity and is coupled to belts of the engine in place of a mechanical air conditioning compressor;
- an alternate power unit comprising rechargeable batteries electrically coupled to the motor generator unit;
- an electric cooler electrically coupled to both the alternate power unit and the motor generator unit such that when the engine is running electricity is received from the motor generator unit, and when the engine is not running electricity is received from the alternate power unit;
- a temperature sensor for sensing the temperature in the passenger compartment; and
- a controller operably connected to the temperature sensor for monitoring and controlling the temperature within the passenger compartment, and further operably connected to the engine of the vehicle;
- wherein if the temperature within the passenger compartment falls outside of a predetermined range of temperatures, the controller activates a heater or the electric cooler to bring the temperatures within the passenger compartment within the predetermined temperature range; and
- wherein the electric cooler is disposed within an enclosure that is cooled by a low pressure refrigerant line of the electric cooler at least partially disposed within the enclosure.

20. The system of claim 19, wherein electrically-powered lights and accessories of the vehicle are electrically connected to and receive electricity from the alternate power unit and the motor generator unit.

21. The system of claim 19, wherein the controller automatically starts the engine when levels of electrical charge in the batteries of the alternate power unit are detected below a predetermined level.

22. The system of claim 19, wherein cool air from the enclosure is directed to the alternate power unit.

23. The system of claim 19, wherein cool air from the enclosure is directed to a power generating device appurtenant to the exhaust from a catalytic converter of the vehicle or a forced cold air induction manifold of the engine.

24. The system of claim 19, wherein the enclosure is configured to shield electromagnetic signals and noise emissions.

25. The system of claim 19, wherein a high pressure refrigerant line of the electric cooler is disposed outside of the enclosure.

26. The system of claim 19, wherein the controller automatically shuts off the engine when a transmission lever of the vehicle is placed in a park position.

27. The system of claim 25, wherein the controller automatically restarts the engine when an accelerator pedal of the vehicle is depressed.

28. The system of claim 19, wherein the motor generator unit supplies power to a crankshaft of the engine.

29. The system of claim 19, including a living occupant sensor for sensing that a living occupant is within the passenger compartment.

* * * * *